US010026509B2

(12) United States Patent
Powers et al.

(10) Patent No.: US 10,026,509 B2
(45) Date of Patent: Jul. 17, 2018

(54) LOW BANDWIDTH MEDIA STREAM TRANSMISSION

(71) Applicant: Architecture Technology Corporation, Minneapolis, MN (US)

(72) Inventors: Judson Powers, Ithaca, NY (US); Tyler Mitchell, Ithaca, NY (US); Daniel James Tingstrom, Ithaca, NY (US); Robert A. Joyce, Ithaca, NY (US)

(73) Assignee: Architecture Technology Corporation, Minneapolis, MN (US)

( * ) Notice: Subject to any disclaimer, the term of this patent is extended or adjusted under 35 U.S.C. 154(b) by 121 days.

(21) Appl. No.: 15/174,704

(22) Filed: Jun. 6, 2016

(65) Prior Publication Data
US 2017/0177821 A1 Jun. 22, 2017

Related U.S. Application Data

(60) Provisional application No. 62/269,838, filed on Dec. 18, 2015.

(51) Int. Cl.
G11B 27/031 (2006.01)
G16H 80/00 (2018.01)
(Continued)

(52) U.S. Cl.
CPC .......... *G16H 80/00* (2018.01); *G11B 27/031* (2013.01); *H04N 5/272* (2013.01);
(Continued)

(58) Field of Classification Search
None
See application file for complete search history.

(56) References Cited

U.S. PATENT DOCUMENTS

2009/0016603 A1* 1/2009 Rossato ............... G06T 7/12
382/173
2011/0305150 A1* 12/2011 Haver .................. H04L 43/106
370/252
(Continued)

OTHER PUBLICATIONS

Poropatich, "TATRC's Strategy for the Research and Development of Mobile Health Applications", retrieved from the internet http://reboot.fcc.gov/c/document_library/get_file?uuid=8ac18153-1b96-4e14-958c-9538a7fc272c&groupId=19001, Jul. 26, 2010, 12 pp.
(Continued)

*Primary Examiner* — Eileen M Adams
(74) *Attorney, Agent, or Firm* — Shumaker & Sieffert, P.A.

(57) ABSTRACT

In general, this disclosure describes media stream transmission techniques for a field computing device and a central computing device. The central computing device may capture an image of a local background environment. The central computing device may record a first media stream that includes at least a portion of the image of the background environment and at least one movement of at least one object through the background environment. The central computing device may remove the image of the background environment from the first media stream to create a second media stream that includes the movement of the object through the background environment without the image of the background environment. The second media stream may also include timing information that can be synchronized to timing information for a media stream originating at the field computing device such that the second media stream may be superimposed on the field media stream.

40 Claims, 5 Drawing Sheets

(51) Int. Cl.
  *H04N 21/2343* (2011.01)
  *H04N 21/8547* (2011.01)
  *H04N 5/272* (2006.01)
  *H04N 21/414* (2011.01)
  *H04N 21/234* (2011.01)
  *H04N 21/462* (2011.01)

(52) U.S. Cl.
  CPC .............. *H04N 21/23418* (2013.01); *H04N 21/234372* (2013.01); *H04N 21/41407* (2013.01); *H04N 21/4622* (2013.01); *H04N 21/8547* (2013.01)

(56) References Cited

U.S. PATENT DOCUMENTS

| | | | | |
|---|---|---|---|---|
| 2014/0153773 A1* | 6/2014 | Gupta | ................. | G06K 9/6202 |
| | | | | 382/103 |
| 2015/0156555 A1* | 6/2015 | Putterman | ......... | H04N 5/44591 |
| | | | | 725/43 |
| 2015/0288933 A1* | 10/2015 | Iversen | ................. | G06F 3/147 |
| | | | | 348/14.07 |
| 2017/0035330 A1* | 2/2017 | Bunn | ................. | A61B 5/1128 |

OTHER PUBLICATIONS

Gilbert, "First Responder Medical Information Exchange and Telemedicine over Tactical Radio Networks", retrieved from the internet, http://www.abstractsonline.com/plan/ViewAbstract.aspx?mID=2885&sKey=7fc33465-d67b-4f60-a795-fc877c8cfdb9&cKey=a647460e-6ae3-4131-9429-bb4f23a501e0&mKey=%7B36FB8B6A-932F-4EDB-A20A-A9448F2863D0%7D, retreived on May 6, 2016, 3pp.

Shenai, et al., "Virtual interactive presence and augmented reality (VIPAR) for remote surgical assistance", retrieved from the internet, http://www.ncbi.nlm.nih.gov/pubmed/21304333, Mar. 2011, 2pp.

SBIR STTR America's Seed Fund, "TELTAN: TELemedcine over a TActical Network", Award Year: 2015, retrieved from the internet https://www.sbir.gov/sbirsearch/detail/869291, retrieved on May 26, 2016, 2 pp.

* cited by examiner

LOW BANDWIDTH MEDIA STREAM TRANSMISSION

This application claims the benefit of U.S. Provisional Application No. 62/269,838, filed Dec. 18, 2015, the entire content of which is incorporated herein by reference.

TECHNICAL FIELD

The disclosure relates to capturing, editing, and transmitting media streams.

BACKGROUND

In general, digital image editing techniques are complicated, processing-heavy techniques where the edited images require more blocks of a storage device than the original image. Further, digital image editing tends to require an abundance of user input to edit an image to the user's liking. This issue is only exacerbated when applied to video editing, as edits must be made to each frame unless a universal edit, such as a color scheme change, is made.

One example where image editing techniques may be applied is with a combat medic in a battlefield. Combat medics can quickly be overcome with the variety and number of injuries received by fellow warfighters. Warfighters are being pushed further and further afield, leaving them outside the range of medical experts. Virtual Interactive Presence and Augmented Reality (VIPAR) systems already in place have shown great potential in alleviating these problems, but these system require too many prerequisites to use in the field. Expensive and specialized pieces of hardware are an additional strain on warfighters, and often times require supplemental training. Systems designed and tested on broadband speed, high fidelity networks are unsuitable for the tumultuous nature of a joint tactical radio system (JTRS) network.

SUMMARY

In general, the disclosure this disclosure describes media stream transmission techniques for a field computing device and a central computing device. For instance, a field computing device may capture a first media stream, wherein the first media stream includes timing information. The field computing device may then send the first media stream to a central computing device. The central computing device may capture an image of a background environment, wherein the background environment is local to the central computing device. The central computing device may then record a second media stream, wherein the second media stream includes at least a portion of the image of the background environment, and wherein the second media stream further includes at least one movement of a representation of at least one object through the background environment. The central computing device may then remove the image of the background environment from the second media stream to create a third media stream, wherein the third media stream includes the at least one movement of the at least one object through the background environment without the image of the background environment. The third media stream may also include timing information that can be synchronized to the timing information of the first media stream. The central computing device may send the third media stream to the field computing device. Finally, the field computing device may superimpose the third media stream on the first media stream, wherein the superimposing is based at least in part on synchronizing the timing information of the third media stream with the timing information of the first media stream.

In one example, the disclosure is directed to a method comprising capturing, by a central computing device, an image of a background environment, wherein the background environment is local to the central computing device, recording, by the central computing device, a first media stream, wherein the first media stream includes at least a portion of the image of the background environment, and wherein the first media stream further includes at least one movement of a representation of at least one object through the background environment, and removing, by the central computing device, the image of the background environment from the first media stream to create a second media stream, wherein the second media stream includes the at least one movement of the at least one object through the background environment without the image of the background environment.

In another example, the disclosure is directed to a device comprising a camera and one or more processors configured to capture, using the camera, an image of a background environment, wherein the background environment is local to the central computing device, record, using the camera, a first media stream, wherein the first media stream includes at least a portion of the image of the background environment, and wherein the first media stream further includes at least one movement of a representation of at least one object through the background environment, and remove the image of the background environment from the first media stream to create a second media stream, wherein the second media stream includes the at least one movement of the at least one object through the background environment without the image of the background environment.

In another example, the disclosure is directed to an apparatus comprising means for capturing an image of a background environment, wherein the background environment is local to the central computing device, means for recording a first media stream, wherein the first media stream includes at least a portion of the image of the background environment, and wherein the first media stream further includes at least one movement of at least one object through the background environment, and means for removing the image of the background environment from the first media stream to create a second media stream, wherein the second media stream includes the at least one movement of the at least one object through the background environment without the image of the background environment.

In another example, the disclosure is directed to a computer-readable medium storing instructions that, when executed, cause one or more processors of a central computing device to capture an image of a background environment, wherein the background environment is local to the central computing device, record a first media stream, wherein the first media stream includes at least a portion of the image of the background environment, and wherein the first media stream further includes at least one movement of a representation of at least one object through the background environment, and remove the image of the background environment from the first media stream to create a second media stream, wherein the second media stream includes the at least one movement of the at least one object through the background environment without the image of the background environment.

In another example, the disclosure is directed to a method comprising capturing, by a field computing device, a first media stream, wherein the first media stream includes timing information, sending, by the field computing device and to a central computing device, the first media stream, after sending the first media stream, receiving, by the field computing device and from the central computing device, a second media stream, wherein the second media stream includes at least one movement of a representation of at least one object without any images of a background environment of the at least one object, and wherein the second media stream further includes timing information corresponding to the timing information of the first media stream, and superimposing, by the field computing device, the second media stream on the first media stream, wherein the superimposing is based at least in part on synchronizing the timing information of the second media stream with the timing information of the first media stream.

In another example, the disclosure is directed to a device comprising a camera and one or more processors configured to capture, using the camera, a first media stream, wherein the first media stream includes timing information, send, to a central computing device, the first media stream, after sending the first media stream, receive, from the central computing device, a second media stream, wherein the second media stream includes at least one movement of a representation of at least one object without any images of a background environment of the at least one object, and wherein the second media stream further includes timing information corresponding to the timing information of the first media stream, and superimpose the second media stream on the first media stream, wherein the superimposing is based at least in part on synchronizing the timing information of the second media stream with the timing information of the first media stream.

In another example, the disclosure is directed to an apparatus comprising means for capturing a first media stream, wherein the first media stream includes timing information, sending, by the field computing device and to a central computing device, the first media stream, after sending the first media stream, means for receiving, from the central computing device, a second media stream, wherein the second media stream includes at least one movement of a representation of at least one object without any images of a background environment of the at least one object, and wherein the second media stream further includes timing information corresponding to the timing information of the first media stream, and means for superimposing the second media stream on the first media stream, wherein the superimposing is based at least in part on synchronizing the timing information of the second media stream with the timing information of the first media stream.

In another example, the disclosure is directed to a computer-readable storage medium storing instructions that, when executed, cause one or more processors of a field computing device to capture a first media stream, wherein the first media stream includes timing information, send, to a central computing device, the first media stream, after sending the first media stream, receive, from the central computing device, a second media stream, wherein the second media stream includes at least one movement of a representation of at least one object without any images of a background environment of the at least one object, and wherein the second media stream further includes timing information corresponding to the timing information of the first media stream, and superimpose the second media stream on the first media stream, wherein the superimposing is based at least in part on synchronizing the timing information of the second media stream with the timing information of the first media stream.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
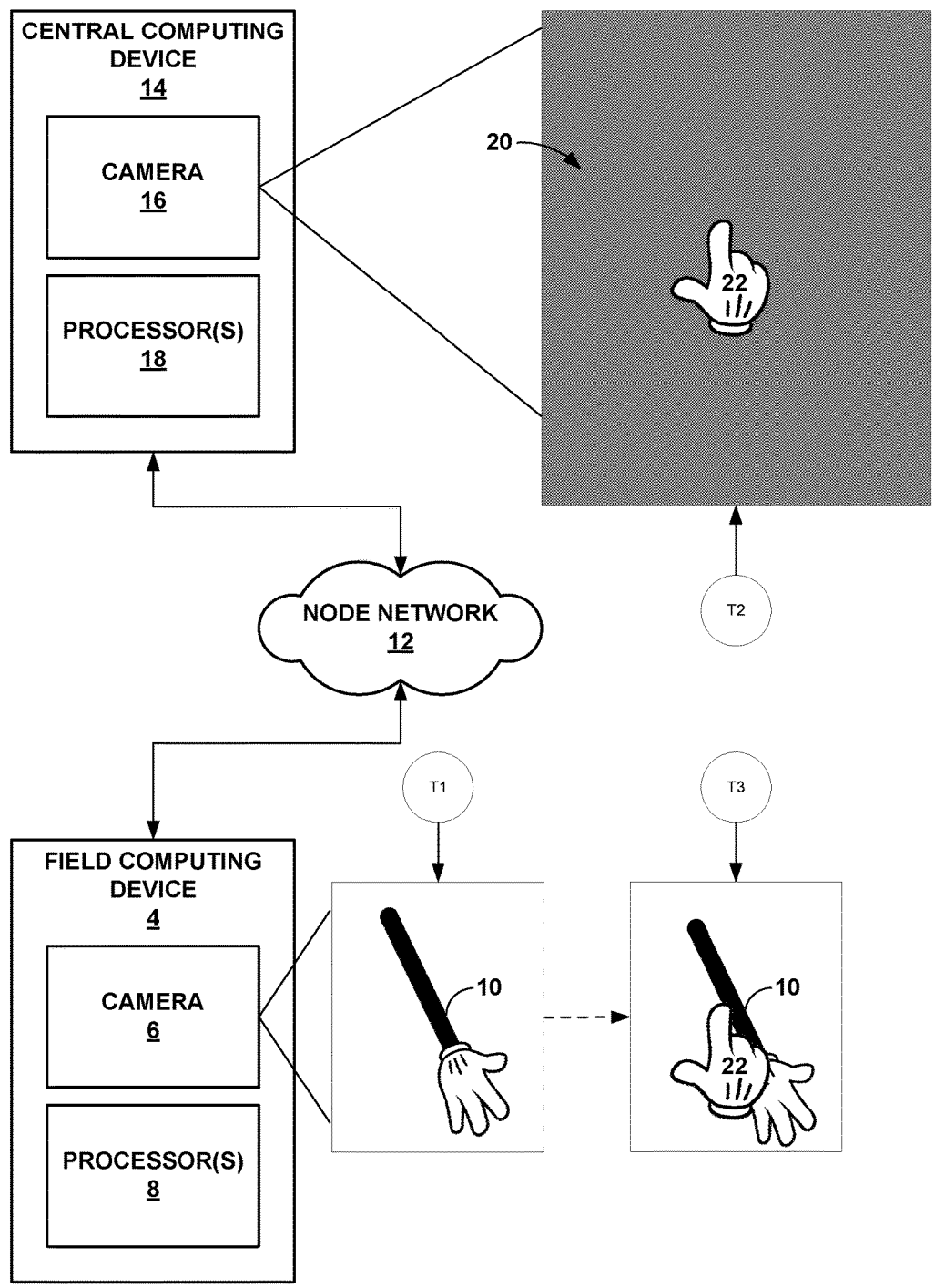
FIG. 1 is a block diagram illustrating an example of media stream transmissions between a field computing device and a central computing device, in accordance with one or more techniques of this disclosure.

In general, this disclosure describes a system for transmitting media streams in a low-bandwidth environment between a field computing device and a central computing device. In many instances, media stream transmissions must over networks that can only transmit data packets with a low bandwidth. As such, sending a full media stream over such a network can be slow and lead to dropped packets during the transmission. As one non-limiting example, if a field medic requires assistance from a remote expert, the expert would typically move themselves or a pointer object in front of a green screen such that the expert may point to portions of a received video containing an injury. However, the full video of the pointer object and the received media stream may need to be sent to the field medic, incurring delays from a large file transmission over the low-bandwidth network. When a field medic requires assistance, any delay or missing portions of an instruction video may lead to further health deterioration. For the purposes of this disclosure, a media stream may be any transmission of data between two computing devices. For instance, a media stream may include video data. In other instances, a media stream may, further or alternatively, include image data, audio data, or textual data. For example, a media stream may include video data and textual data corresponding to a heart rate and a blood pressure.

In cases such as these, for example, the ability for a medical expert to see medical problems in real time, and offer assistance based on what the expert sees, may assist in saving numerous lives. Virtual Interactive Presence and Augmented Reality (VIPAR) systems offer a possible solution to this. However, existing VIPAR systems have a number of flaws. Expensive and specialized hardware is the highest bar of entry for existing VIPAR systems. For instance, loading warfighters with additional hardware that requires special precautions in transit makes current systems difficult to deploy. Existing VIPAR systems further require low-latency, high-bandwidth networks to function properly. Tactical networks, on the other hand, may have limited bandwidth with high latency and intermittent loss of service. The practical limitations of tactical networks mean that an application may need to be developed with these limitations in mind. Otherwise, the resulting video stream may be delayed, choppy, and nonfunctional. Traditionally, video overlay systems require a flat background color in order to capture the correct image, which is rarely an option in the field, and even when it is possible to achieve, it can require extensive preparation time to set up. Further problems with hardware, bandwidth, and video systems have made adoption of VIPAR systems in the field very difficult.

In accordance with techniques of this disclosure, a central computing device may remove background images from a video, leaving only the portion of the original media stream that contains the pointer object moving through the environment. The altered media stream may include timing information such that the field computing device can locally superimpose the altered media stream on top of the initial media stream captured by the field computing device that is already stored on the field computing device itself. By performing this operation locally, the field computing device is not constrained by the low-bandwidth network. By cutting the size of the file being transmitted across the network, the transmission may be more efficiently and completely delivered.

This transmission system can be utilized for telemedicine over a tactical network (TELTAN). As described herein, TELTAN is a multi-platform VIPAR system emphasizing operation in low-fidelity networks, with low-bandwidth overhead. By operating with a low-bandwidth overhead, TELTAN may provide efficiency when run on a tactical network. A simple interface may allow for easy set up and connections, even under extreme conditions. Being deployable across multiple systems may remove the necessity for specialized hardware, and the easy-to-follow interface may require minimal training, lowering monetary costs, as well as easing field deployment. Organizations like civilian hospitals may benefit from immediate access to an expert, or emergencies in isolated areas where medical attention is out of immediate reach. Additionally, remote repairs of specialized hardware may be far more easily managed, rather than having to send an expert to the field.

Techniques of this disclosure may provide a video streaming system that allows a video stream to be sent to, e.g., an expert who can place their hands into the video stream, which is then sent back to the source. These techniques may be used over low-bandwidth, low-fidelity networks and run with low-system requirements, including on tablet computers and mobile phones. These techniques may produce quality images provided by onboard devices, like mobile phone cameras. Further, techniques of this disclosure do not have a Chroma Key (e.g., green screen or other) requirement, which may not always be an option in the field.

In various examples, a device carried by a warfighter in the field may be referred to as the "field computing device", and a device held by the expert, kept at a base of operations, may be referred to as the "central computing device." The field and central computing devices will connect, allowing for video captured by the field device to be streamed to the central computing device. Upon receiving the video, the expert may be able to "insert" their hands into the video stream. Information about the hands will then be sent back to the field computing device.

FIG. 1 is a block diagram illustrating an example of media stream transmissions between a field computing device 4 and a central computing device 14, in accordance with one or more techniques of this disclosure. Field computing device 4 is described below, for purposes of illustration only, as a smartphone. However, in some examples, field computing device 4 may be a computerized watch (e.g., a smart watch), computerized eyewear, computerized headwear, other types of wearable computing devices, a tablet computer, a personal digital assistant (PDA), a laptop computer, a gaming system, a media player, a television platform, an automobile navigation system, a digital camera, or any other type of mobile and/or non-mobile computing device that is configured to perform a media operation as described herein.

Field computing device 4 may include an input component. For instance, field computing device 4 may be configured to receive input from a user through tactile, audio, or video feedback. Examples of input components include a display component, a mouse, a keyboard, a camera, a microphone or any other type of device for detecting input from a user. In some examples, a display component includes a touch-sensitive screen. Field computing device 4 may also include a structure capable of receiving a radio signal. For instance, field computing device 4 may include a radio antenna, a radio receiver, a communication receiver, or a scanner, among other things. In the non-limiting example of FIG. 1, field computing device 4 includes camera 6, which may be configured to capture moving images, still images, and, in some instances where camera 6 includes a microphone, audio data.

Field computing device 4 may further include one or more processors 8. One or more processors 8, in one example, are configured to implement functionality and/or process instructions for execution within field computing device 4. For example, processors may be capable of processing instructions stored in a storage device of field computing device 4. Examples of processors 8 may include, any one or more of a microprocessor, a controller, a digital signal processor (DSP), an application specific integrated circuit (ASIC), a field-programmable gate array (FPGA), or equivalent discrete or integrated logic circuitry.

Central computing device 14 is described below as a desktop computer. However, in some examples, central computing device 14 may be a smartphone, a computerized watch (e.g., a smart watch), computerized eyewear, computerized headwear, other types of wearable computing devices, a tablet computer, a personal digital assistant (PDA), a laptop computer, a gaming system, a media player, an e-book reader, a television platform, an automobile navigation system, a digital camera, or any other type of mobile and/or non-mobile computing device that is configured to perform a media operation as described herein.

Central computing device 14 may include an input component. For instance, central computing device 14 may be configured to receive input from a user through tactile, audio, or video feedback. Examples of input components include a display component, a mouse, a keyboard, a camera, a microphone or any other type of device for detecting input from a user. In some examples, a display component includes a touch-sensitive screen. Central computing device 14 may also include a structure capable of receiving a radio signal. For instance, central computing device 14 may include a radio antenna, a radio receiver, a communication receiver, or a scanner, among other things. In the example of FIG. 1, central computing device 14 includes camera 16, which may be configured to capture moving images, still images, and, in some instances where camera 16 includes a microphone, audio data.

Central computing device 14 may further include one or more processors 18. One or more processors 18, in one example, are configured to implement functionality and/or process instructions for execution within central computing device 14. For example, processors may be capable of processing instructions stored in a storage device of central computing device 14. Examples of processors 18 may include, any one or more of a microprocessor, a controller, a digital signal processor (DSP), an application specific integrated circuit (ASIC), a field-programmable gate array (FPGA), or equivalent discrete or integrated logic circuitry.

Field computing device 4 and central computing device 14 may be capable of sending media transmissions across node network 12. Node network 12 may represent any communication network, such as a packet-based digital network. In other examples, node network 12 may represent any wired or wireless network such as the Internet, a private corporate intranet, or a PSTN telephonic network. Node network 12 may include both wired and wireless networks as well as both public and private networks. Field computing device 4 and central computing device 14 may each contain one or more devices for accessing node network 12, such as modems, switches and the like. Network access devices (e.g., a router and firewall) may couple the private network to node network 12 for communication with computing devices associated with central computing device 14. In some examples, node network 12 may include a system of interconnected radio towers that receive a media stream from field computing device 4, send the media stream to one or more other radio towers, and, ultimately, forward the media stream to central computing device 14.

In accordance with techniques of the current disclosure, at time T1, field computing device 4 may capture a first media stream. The first media stream includes timing information. The timing information may include a time that the media stream begins, such as a time of day or a 0:00:00 indication, and a time that the media stream ends, such as a time of day later than the first time of day or a time in the form of #:##:##, wherein the #'s indicate numbers describing the length of the first media stream. The first media stream may include object 10, which may, in certain non-limiting examples, be a body part containing an injury or an ailment that is to be treated medically. In the example of FIG. 1, object 10 is a subject's arm that may, for instance, be dislocated. Field computing device 4 may send the first media stream to central computing device 14 across node network 12.

Central computing device 14 may receive the first media stream at a remote location, where a medical expert may analyze the injury and determine a medical treatment that must be performed on object 10. To respond, central computing device 14 may first capture an image of background environment 20. Background environment 20 may be local to central computing device 14. Background environment 20 may be any background environment, such as a solid-colored or patterned background "stage" or a general room containing various objects, among other things.

Central computing device 14 may record a second media stream. The second media stream may include at least a portion of the image of background environment 20 and at least one movement of object 22 (e.g., image of the medical expert's hand) through background environment 20. For instance, after analyzing the injury to object 10, a medical expert may determine that a portion of object 10 may need to be moved or set in a specific manner, or that medical treatment must be provided to a specific portion of object 10. In the example of FIG. 1, where the subject's arm is dislocated, object 22 may move in a way that corresponds to the movement that must occur to re-set the subject's arm into the correct socket and how to prepare a sling for the arm to be cradled until further medical treatment can be provided.

Central computing device 14 may remove the image of background environment 20 from the second media stream to create a third media stream. The third media stream, accordingly, may only include the at least one movement of object 22 through background environment 20 without actually including the image of background environment 20. By removing the image of background environment 20, the third media stream will have a smaller size than the second media stream, allowing it to cross low-bandwidth node network 12 quicker and more efficiently.

The image of background environment 20 may be removed in any way suitable for the techniques described herein. For instance, if background environment 20 is a solid color, central computing device 14 may remove any pixel from the second media stream that matches or approximately matches (taking into account shading) the color of the pixels in the image of background environment 20. If background environment 20 is a patterned background or a general room, the color-removal process may be repeated for each color found in the image of background environment 20. In other examples, central computing device 14 may compute a depth at which background environment 20 lies in the image of background environment 20. Central computing device 14 may then remove all objects from the second media stream found at that depth, leaving only the newly introduced object 22 in the third media stream. These are merely examples of how background environment 20 may be removed from the third media stream. Any other technique available that results in the removal of background environment 20 from the second media stream may be utilized in accordance with the techniques of the current disclosure.

For instance, in another example of removing the image of background environment 20 from the second media stream, central computing device 14 may store a set of one or more object patterns. Each object pattern in the set of one or more object patterns may be one of a possible shape or a possible color of a possible configuration of the at least one object. Central computing device 14 may determine one or more portions of the first media stream that match an object pattern of the set of one or more object patterns. For each frame of the at least one frame of the first media stream, central computing device 14 may remove each pixel of the first media stream that is outside of the one or more portions that match the object pattern. For example, central computing device 14 may store different possible shapes and colors of hands. Central computing device 14 may attempt to find a portion of the second media stream that matches one of the object patterns containing possible shapes and colors of hands. Determining that the found portion is a hand, central computing device 14 may remove the pixels in the second media stream that are outside of the found portion, leaving only the hand in the second media stream.

In another example of removing the image of background environment 20 from the second media stream, central computing device 14 may, for each frame of at least one frame of the second media stream, compare the respective frame of the first media stream to the image of the background environment. Central computing device 14 may then remove each pixel of the second media stream with a color value equal to a color value of a corresponding pixel value in the image of the background environment. For instance, if camera 16 is in a fixed position, the background environment will not change between the image of the background environment and the filming of the second media stream. As such, if object 22 is in the middle of the second media stream, the pixel in the top-left corner of the second media stream may have a color value equal to the pixel in the top-left corner of the image of the background environment. As such, this pixel may be removed. Removing each matching pixel from each frame of the second media stream may leave only object 22 in the second media stream.

Central computing device 14 may include timing information in the third media stream such that the timing information of the third media stream can be synchronized to the timing information of the first media stream. The timing information may include a time corresponding to the time that the first media stream begins, such as the time of day or the 0:00:00 indication, and a time corresponding to the time that the first media stream ends, such as the time of day later than the first time of day or the time in the form of #:##:##, wherein the #'s indicate numbers describing the length of the first media stream.

At time T3, field computing device 4 may receive, from central computing device 14, the third media stream. As described above, the third media stream may include at least one movement of object 22 without any images of background environment 20. The third media stream may further include timing information corresponding to the timing information of the first media stream.

Field computing device 4, with the received third media stream and the originally captured first media stream, may superimpose the received third media stream on the first media stream. Field computing device 4 may perform the superimposing based at least in part on synchronizing the timing information of the third media stream with the timing information of the first media stream. For instance, if the timing information of the third media stream includes a start time in an hour-minute-second #:##:## format, field computing device 4 may superimpose the third media stream on top of the first media stream at a point in the first media stream that equals the start time of the third media stream. For instance, the third media stream may start at 0:00:06, meaning six seconds into the first media stream. As such, at the six second mark of the first media stream, field computing device 4 may superimpose the third media stream on top of the first media stream, playing both media streams simultaneously until both media streams end. In some examples, when the third media stream contains audio, field computing device 4 may further replace any audio in the first media stream with the audio of the third media stream.

The superimposed video provides the field computing device with a treatment for object 10. For instance, in the example of FIG. 1, where object 10 is a dislocated arm, object 22 would be overlaid on top of object 10, and would appear to move along object 10 in a way necessary for treatment of the dislocated arm to occur, such as a movement to re-set the dislocated arm and to place the arm in a sling. By performing the superimposing locally on field computing device 4 rather than field computing device 4 receiving a full media stream of the treatment over low-bandwidth node network 12, field computing device 4 is able to receive a quality instructional treatment in a shorter time than if field computing device 4 waited for the entirety of a full media stream to be received.

Figure 2:
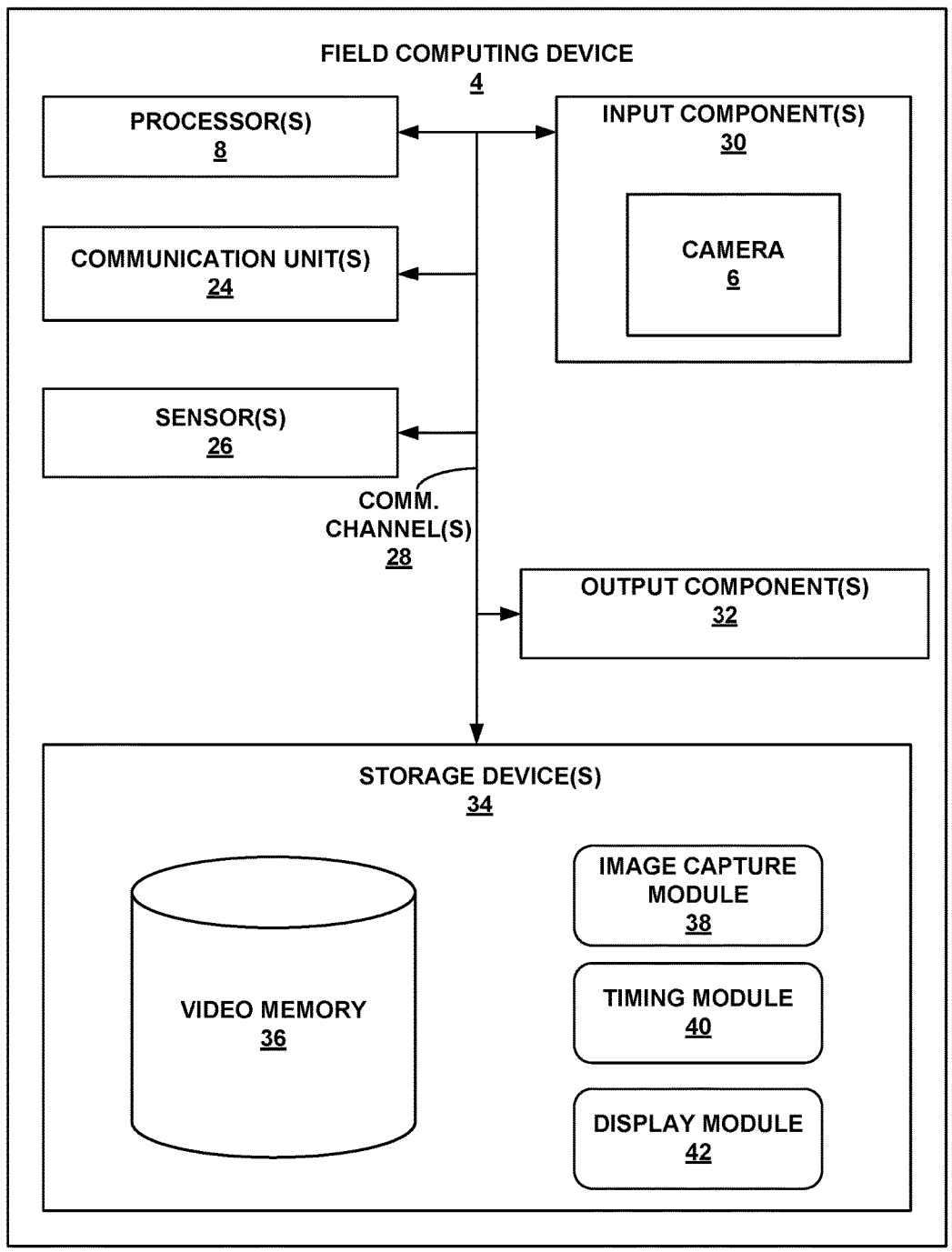
FIG. 2 is a block diagram illustrating an example field computing device, in accordance with one or more techniques of this disclosure.

FIG. 2 is a block diagram illustrating an example field computing device 4, in accordance with one or more techniques of this disclosure. Field computing device 4 of FIG. 2 is described below as one particular example of field computing device 4 shown in FIG. 1. FIG. 2 illustrates only one particular example of field computing device 4, and many other examples of field computing device 4 may be used in other instances and may include a subset of the components included in example field computing device 4 or may include additional components not shown in FIG. 2.

For example, field computing device 4 may include a battery to provide power to the components of field computing device 4. Similarly, the components of field computing device 4 shown in FIG. 2 may not be necessary in every example of field computing device 4. For example, in some configurations, field computing device 4 may not include communication units 24.

As shown in the example of FIG. 2, field computing device 4 includes one or more processors 8, one or more input components 30, one or more communication units 24, one or more output components 32, one or more sensors 26, and one or more storage devices 34. Input components 30 may include camera 6.

Output components 32, in some examples, are configured to provide output to a user using tactile, audio, or video stimuli. Output components 32, in one example, include an electronic display, a loudspeaker, or any other type of device for converting a signal into an appropriate form understandable to humans or machines. The electronic display may be a liquid crystal display (LCD) or organic light-emitting diode (OLED) part of a touch screen, may be a non-touchscreen direct view display component such as a cathode ray tube (CRT), light-emitting diode (LED), LCD, or OLED. The display component may also be a projector instead of a direct view display.

Input components 30, in some examples, is configured to receive input from a user through tactile, audio, or video feedback. Examples of input components 30 include a display component, a mouse, a keyboard, a camera, a microphone or any other type of device for detecting input from a user. In some examples, a display component includes a touch-sensitive screen. Input component 30 may, for instance, include camera 6. In some instances, camera 6 may be configured to record an image or a video stream. In some further instances, camera 6 may also include a microphone to capture audio data.

One or more storage devices 34 of field computing device 4 include video memory 36, image capture module 38, timing module 40, and display module 42. One or more storage devices 34 may be configured to store information within field computing device 4 during operation. Storage device 34, in some examples, is described as a computer-readable storage medium. In some examples, storage device 34 and video memory 36 is a temporary memory, meaning that a primary purpose of storage device 34 and video memory 36 is not long-term storage. Storage device 34 and video memory 36, in some examples, are described as volatile memories, meaning that storage device 34 and video memory 36 do not maintain stored contents when the computing device is turned off. Examples of volatile memories include random access memories (RAM), dynamic random access memories (DRAM), static random access memories (SRAM), and other forms of volatile memories known in the art. In some examples, storage device 34 is used to store program instructions for execution by processors 8.

Storage devices 34 and video memory 36, in some examples, also include one or more computer-readable storage media. Storage devices 34 and video memory 36 may be configured to store larger amounts of information than volatile memory. Storage devices 34 and video memory 36 may further be configured for long-term storage of information. In some examples, storage devices 34 and video memory 36 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Communication channels 28 may interconnect each of the components 8, 24, 26, 30, 6, 32, 34, 36, 38, 40, and 42 for inter-component communications (physically, communicatively, and/or operatively). In some examples, communication channels 28 may include a system bus, a network connection, an inter-process communication data structure, or any other method for communicating data.

One or more communication units 24 of field computing device 4 may communicate with external devices, such as a server device, via one or more wired and/or wireless networks by transmitting and/or receiving network signals on the one or more networks. Communication units 24 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, field computing device 4 utilizes communication units 24 to wirelessly communicate with another computing device that is operably coupled to field computing device 4, such as central computing device 14 of FIG. 1.

One or more processors 8, in one example, are configured to implement functionality and/or process instructions for execution within field computing device 4. For example, processors 8 may be capable of processing instructions stored in storage device 34. Examples of processors 8 may include, any one or more of a microprocessor, a controller, a digital signal processor (DSP), an application specific integrated circuit (ASIC), a field-programmable gate array (FPGA), or equivalent discrete or integrated logic circuitry.

In some examples, field computing device 4 may include one or more sensors 26. One or more of sensors 26 may measure one more measurands. Examples of one or more of sensors 26 may include one or more position sensors (e.g., a global positioning system (GPS) sensor, an indoor positioning sensor, or the like), one or more motion/orientation sensors (e.g., an accelerometer, a gyroscope), a light sensor, a temperature sensor, a pressure (or grip) sensor, a physical switch, a proximity sensor, and one or more bio-sensors that can measure properties of the skin/blood, such as alcohol, blood sugar, heart rate, and/or perspiration level.

In accordance with techniques of the current disclosure, image capture module 38 of field computing device 4 may capture a first media stream and store the first media stream in video memory 36. The first media stream includes timing information. The timing information may include a time that the media stream begins, such as a time of day or a 0:00:00 indication, and a time that the media stream ends, such as a time of day later than the first time of day or a time in the form of #:##:##, wherein the #'s indicate numbers describing the length of the first media stream. The first media stream may include representation of an object, which may, in certain non-limiting examples, be a body part containing an injury or an ailment that is to be treated medically. In the example of FIG. 2, for purposes of description only, the object may be a subject's leg that may, for instance, be gashed. Image capture module 38 of field computing device 4 may send the first media stream to a central computing device (e.g., central computing device 14 of FIG. 1) across a node network (e.g., node network 12 of FIG. 1).

Field computing device 4 may receive, from the central computing device, a second media stream. The second media stream may include at least one movement of a second object without any images of a background environment. The second media stream may further include timing information corresponding to the timing information of the first media stream.

Display module 42 of field computing device 4, with the received second media stream and the originally captured first media stream stored in video memory 36, may superimpose the received second media stream on the first media stream. Display module 42 of field computing device 4 may perform the superimposing based at least in part on timing module 40 aligning the timing information of the second media stream with the timing information of the first media stream. For instance, if the timing information of the second media stream includes a start time in an hour-minute-second #:##:## format, display module 42 may superimpose the second media stream on top of the first media stream at a point in the first media stream that equals the start time of the second media stream, as determined by timing module 40. For instance, timing module 40 may determine that the second media stream may start at 0:00:06, meaning six seconds into the first media stream. As such, at the six second mark of the first media stream, display module 42 may superimpose the second media stream on top of the first media stream, playing both media streams simultaneously until both media streams end. In some examples, when the second media stream contains audio, display module 42 may further replace any audio in the first media stream with the audio of the second media stream.

In some examples, display module 42 may alter the size of the received second media stream. For instance, display module 42 may resize the received second media stream such that it is in the same aspect ratio as the recorded first media stream.

The superimposed video provides the field computing device with a treatment for object 10. For instance, where the first object is a gashed leg, the second object would be overlaid on top of the gashed leg, and would appear to move along the gashed leg in a way necessary for treatment of the gashed leg to occur, such as a movement to suture the wound. By performing the superimposing locally on field computing device 4 rather than field computing device 4 receiving a full media stream of the treatment over a low-bandwidth node network, field computing device 4 is able to receive a quality instructional treatment in a shorter time than if field computing device 4 waited for the entirety of a full media stream to be received.

Figure 3:
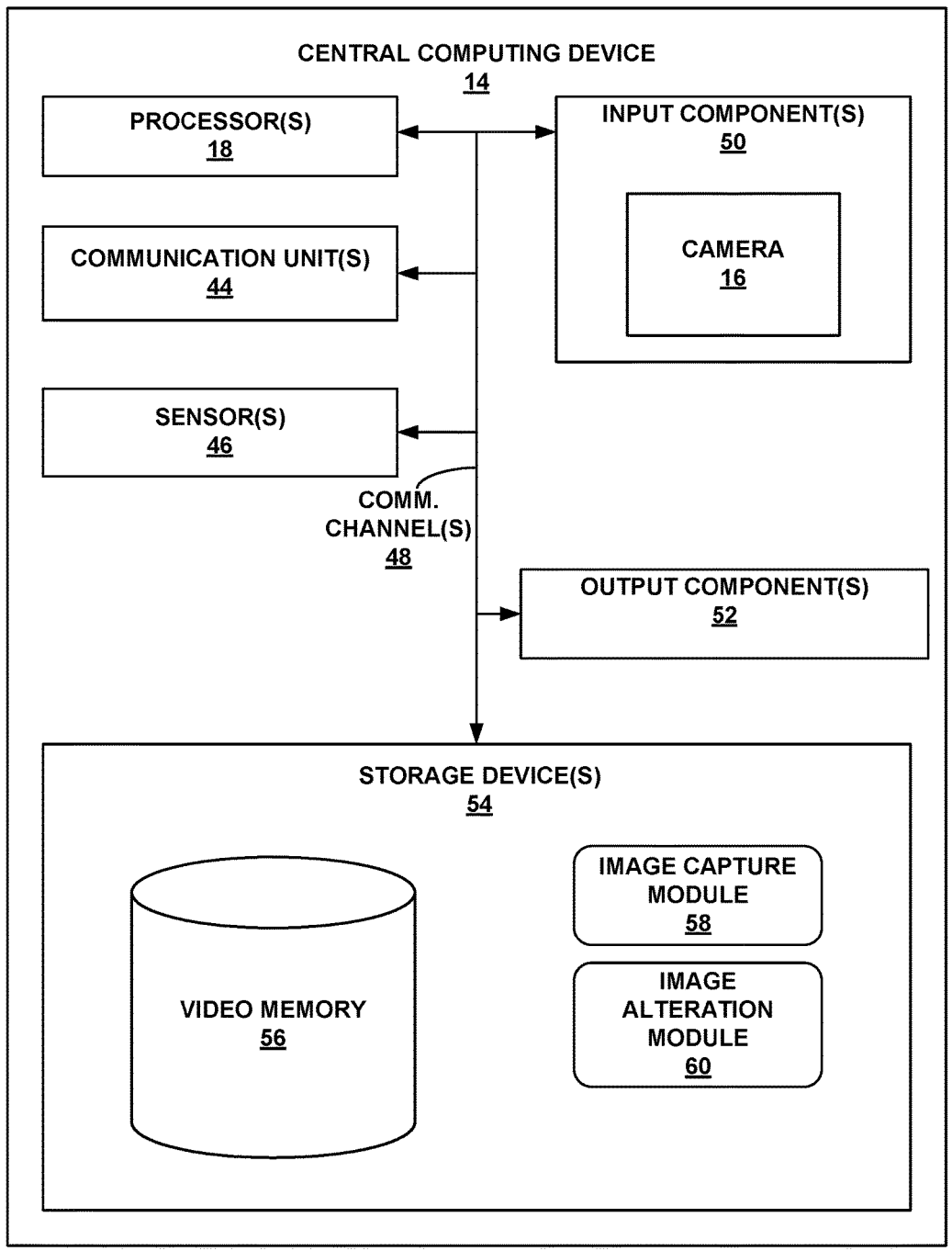
FIG. 3 is a block diagram illustrating an example central computing device, in accordance with one or more techniques of this disclosure.

FIG. 3 is a block diagram illustrating an example central computing device 14, in accordance with one or more techniques of this disclosure. Central computing device 14 of FIG. 3 is described below as one particular example of central computing device 14 shown in FIG. 1. FIG. 3 illustrates only one particular example of central computing device 14, and many other examples of central computing device 14 may be used in other instances and may include a subset of the components included in example central computing device 14 or may include additional components not shown in FIG. 3.

For example, central computing device 14 may include a battery to provide power to the components of central computing device 14. Similarly, the components of central computing device 14 shown in FIG. 3 may not be necessary in every example of central computing device 14. For example, in some configurations, central computing device 14 may not include communication units 44.

As shown in the example of FIG. 3, central computing device 14 includes one or more processors 18, one or more input components 50, one or more communication units 44, one or more output components 52, one or more sensors 46, and one or more storage devices 54. Input components 50 may include camera 16.

Output components 52, in some examples, are configured to provide output to a user using tactile, audio, or video stimuli. Output components 52, in one example, include an electronic display, a loudspeaker, or any other type of device for converting a signal into an appropriate form understandable to humans or machines. The electronic display may be an LCD or OLED part of a touch screen, may be a non-touchscreen direct view display component such as a CRT, LED, LCD, or OLED. The display component may also be a projector instead of a direct view display.

Input components 50, in some examples, is configured to receive input from a user through tactile, audio, or video feedback. Examples of input components 50 include a display component, a mouse, a keyboard, a camera, a microphone or any other type of device for detecting input from a user. In some examples, a display component includes a touch-sensitive screen. Input component 50 may, for instance, include camera 16. In some instances, camera 16 may be configured to record an image or a video stream. In some further instances, camera 16 may also include a microphone to capture audio data.

One or more storage devices 54 of central computing device 14 include video memory 56, image capture module 58, and image alteration module 60. One or more storage devices 54 may be configured to store information within central computing device 14 during operation. Storage device 54, in some examples, is described as a computer-readable storage medium. In some examples, storage device 54 and video memory 56 is a temporary memory, meaning that a primary purpose of storage device 54 and video memory 56 is not long-term storage. Storage device 54 and video memory 56, in some examples, are described as volatile memories, meaning that storage device 54 and video memory 56 do not maintain stored contents when the computing device is turned off. Examples of volatile memories include random access memories (RAM), dynamic random access memories (DRAM), static random access memories (SRAM), and other forms of volatile memories known in the art. In some examples, storage device 54 is used to store program instructions for execution by processors 18.

Storage devices 54 and video memory 56, in some examples, also include one or more computer-readable storage media. Storage devices 54 and video memory 56 may be configured to store larger amounts of information than volatile memory. Storage devices 54 and video memory 56 may further be configured for long-term storage of information. In some examples, storage devices 54 and video memory 56 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Communication channels 48 may interconnect each of the components 18, 44, 46, 50, 16, 52, 54, 56, 58, and 60 for inter-component communications (physically, communicatively, and/or operatively). In some examples, communication channels 48 may include a system bus, a network connection, an inter-process communication data structure, or any other method for communicating data.

One or more communication units 44 of central computing device 14 may communicate with external devices, such as a field computing device, via one or more wired and/or wireless networks by transmitting and/or receiving network signals on the one or more networks. Communication units 44 may include a network interface card, such as an Ethernet card, an optical transceiver, a radio frequency transceiver, or any other type of device that can send and receive information. Examples of such network interfaces may include Bluetooth, infrared signaling, 3G, LTE, and Wi-Fi radios as well as Universal Serial Bus (USB) and Ethernet. In some examples, central computing device 14 utilizes communication units 44 to wirelessly communicate with another computing device that is operably coupled to central computing device 14, such as field computing device 4 of FIG. 1.

One or more processors 18, in one example, are configured to implement functionality and/or process instructions for execution within central computing device 14. For example, processors 18 may be capable of processing instructions stored in storage device 54. Examples of processors 18 may include, any one or more of a microprocessor, a controller, a digital signal processor (DSP), an application specific integrated circuit (ASIC), a field-programmable gate array (FPGA), or equivalent discrete or integrated logic circuitry.

In some examples, central computing device 14 may include one or more sensors 46. One or more of sensors 46 may measure one more measurands. Examples of one or more of sensors 46 may include one or more position sensors (e.g., a global positioning system (GPS) sensor, an indoor positioning sensor, or the like), one or more motion/orientation sensors (e.g., an accelerometer, a gyroscope), a light sensor, a temperature sensor, a pressure (or grip) sensor, a physical switch, a proximity sensor, and one or more biosensors that can measure properties of the skin/blood, such as alcohol, blood sugar, heart rate, and/or perspiration level.

In accordance with techniques of this disclosure, image capture module 58 of central computing device 14 may first capture an image of a background environment (e.g., background environment 20 of FIG. 1), possibly utilizing camera 16. The background environment may be local to central computing device 14. For instance, the background environment may be any background environment, such as a solid-colored or patterned background "stage" or a general room containing various objects, among other things.

Image capture module 58 of central computing device 14 may then record a first media stream, possibly utilizing camera 16. The first media stream may include at least a portion of the image of the previously captured background environment and at least one movement of an object (e.g., image of the medical expert's hand) through said background environment.

Image alteration module 60 of central computing device 14 may remove the image of background environment 20 from the first media stream to create a second media stream. The second media stream, accordingly, may only include the at least one movement of the object through the background environment without actually including the image of the background environment. By removing the image of the background environment, the second media stream will have a smaller size than the first media stream, allowing it to cross a low-bandwidth node network quicker and more efficiently. In some examples, image alteration module 60 may further replace the object in the second media stream with a digital image different than the object. For instance, image alteration module 60 may replace the object in the second media stream with a vector graphic, an arrow graphic, or a low-resolution representation of the object, such as a digital hand or pointer object.

The image of the background environment may be removed from the first media stream in any way suitable for the techniques described herein. For instance, if the background environment is a solid color, image alteration module 60 may detect a pixel color value present in the image of the background environment and remove any pixel from each frame of the first media stream that matches or approximately matches (e.g., taking into account shading) the detected pixel color value of the pixels in the image of the background environment. If the background environment is a patterned background or a general room, the color-removal process may be repeated for each color found in the image of the background environment. In other examples, image alteration module 60 of central computing device 14 may compute a depth at which the background environment lies in the image of the background environment. Image alteration module 60 of central computing device 14 may then remove all objects from the first media stream found at that depth, leaving only the newly introduced object in the second media stream. These are merely examples of how the background environment may be removed from the first media stream. Any other technique available that results in the removal of the background environment from the first media stream may be utilized in accordance with the techniques of the current disclosure.

For instance, in another example of removing the image of background environment 20 from the second media stream, image alteration module 60 may store a set of one or more object patterns. Each object pattern in the set of one or more object patterns may be one of a possible shape or a possible color of a possible configuration of the at least one object. Image alteration module 60 may determine one or more portions of the first media stream that match an object pattern of the set of one or more object patterns. For each frame of the at least one frame of the first media stream, image alteration module 60 may remove each pixel of the first media stream that is outside of the one or more portions that match the object pattern. For example, image alteration module 60 may store different possible shapes and colors of hands. Image alteration module 60 may attempt to find a portion of the second media stream that matches one of the object patterns containing possible shapes and colors of hands. Determining that the found portion is a hand, image alteration module 60 may remove the pixels in the second media stream that are outside of the found portion, leaving only the hand in the second media stream.

In another example of removing the image of background environment 20 from the second media stream, image alteration module 60 may, for each frame of at least one frame of the second media stream, compare the respective frame of the first media stream to the image of the background environment. Image alteration module 60 may then remove each pixel of the second media stream with a color value equal to a color value of a corresponding pixel value in the image of the background environment. For instance, if camera 16 is in a fixed position, the background environment will not change between the image of the background environment and the filming of the second media stream. As such, if object 22 is in the middle of the second media stream, the pixel in the top-left corner of the second media stream may have a color value equal to the pixel in the top-left corner of the image of the background environment. As such, this pixel may be removed. Removing each matching pixel from each frame of the second media stream may leave only object 22 in the second media stream.

In some examples, central computing device 14 may receive a field media stream from a field computing device (e.g., field computing device 4 of FIG. 1). The field media stream may include timing information. In such examples, image capture module 58 of central computing device 14 may include timing information in the second media stream such image alteration module 60 may align the timing information of the second media stream to the timing information of the field media stream. The timing information may include a time corresponding to the time that the field media stream begins, such as the time of day or the 0:00:00 indication, and a time corresponding to the time that the field media stream ends, such as the time of day later than the first time of day or the time in the form of #:##:##, wherein the #'s indicate numbers describing the length of the field media stream. In some instances, the timing information may instead or additionally include frame numbers. Central computing device 14 may then send the second media stream and the timing information of the second media stream to the field computing device. In instances where image capture module 58 utilizes a microphone of camera 16 to capture audio data, the second media stream may further include the audio stream containing the captured audio data.

For instance, in aligning the timing information, image alteration module 60 may determine, based at least in part on the timing information of the field media stream, a starting time of the field media stream and an ending time of the field media stream. Image alteration module 60 may then determine a starting time for the second media stream and an ending time for the second media stream. The starting time for the second media stream may be between the starting time of the field media stream and the ending time of the field media stream. Further, the ending time for the second media stream may be after the starting time of the second media stream and before the ending time of the field media stream. As such, the timing information of the second media stream would be within the timing information of the field media stream and using the same time units as the field media stream (e.g., seconds).

In some examples, image alteration module 60 may further alter the size of the second media stream. For instance, image alteration module 60 may resize the second media stream such that the aspect ratio of the second media stream matches an aspect ratio of the field media stream.

In one use case of the above techniques, a medical expert at a remote location may receive a field media stream from a field media device showing an injury, such as a gashed leg. After analyzing the injury to the leg, the medical expert may determine that a portion of the gashed leg may need to be moved or set in a specific manner, or that medical treatment must be provided to a specific portion of the gashed leg. Image capture module 58 of central computing device 14 may capture an image of a background environment that the medical expert will use as the background for the instructional video the medical expert is about to record. Image capture module 58 of central computing device 14 may then record a first media stream of the medical expert moving his/her hands through the background environment, showing how the gashed leg must be sutured. Image alteration module 60 may then remove the image of the background environment from the first media stream to obtain a second media stream that only includes the medical expert's hands moving through space without the image of the background environment. By removing the background environment, the file size will be much smaller than a media stream with the background environment. The smaller file size allows for faster and more efficient transfer of the media stream to the field computing device across a low-bandwidth node network.

Figure 4:
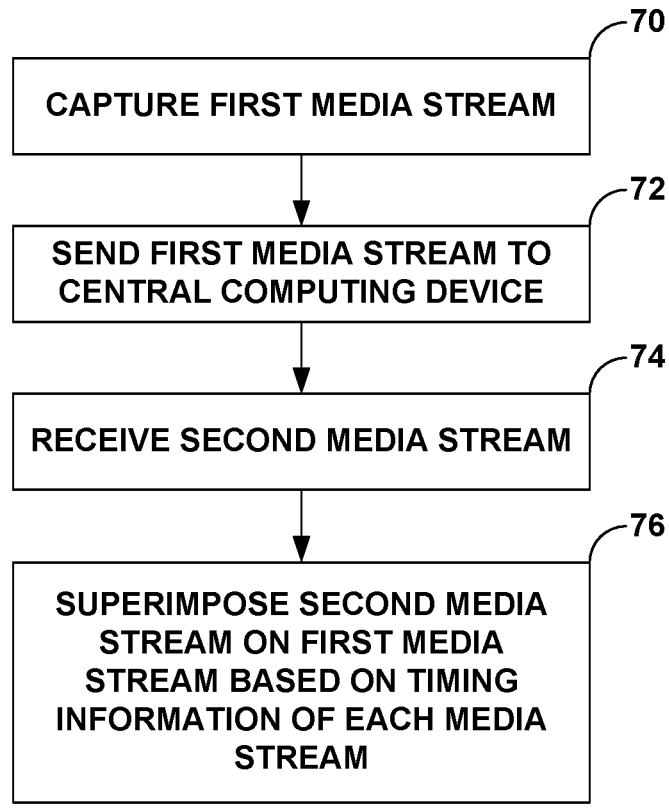
FIG. 4 is a flow diagram illustrating example operations of a field computing device that implements location techniques in accordance with one or more aspects of this disclosure.

FIG. 4 is a flow diagram illustrating example operations of a field computing device that implements location techniques in accordance with one or more aspects of this disclosure. The techniques of FIG. 4 may be performed by one or more processors of a computing device, such as field computing device 4 illustrated in FIG. 1 and/or FIG. 2. For purposes of illustration only, the techniques of FIG. 4 are described within the context of field computing device 4 of FIG. 1, although computing devices having configurations different than that of field computing device 4 may perform the techniques of FIG. 4.

In accordance with techniques of the current disclosure, field computing device 4 may capture (70) a first media stream. The first media stream includes timing information. The timing information may include a time that the media stream begins, such as a time of day or a 0:00:00 indication, and a time that the media stream ends, such as a time of day later than the first time of day or a time in the form of #:##:##, wherein the #'s indicate numbers describing the length of the first media stream. The first media stream may include a representation of an object, which may, in certain non-limiting examples, be a body part containing an injury or an ailment that is to be treated medically. Field computing device 4 may send (72) the first media stream to a central computing device (e.g., central computing device 14 of FIG. 1) across a node network (e.g., node network 12 of FIG. 1).

Field computing device 4 may receive (74), from the central computing device, a second media stream. The second media stream may include at least one movement of a second object without any images of a background environment. The second media stream may further include timing information corresponding to the timing information of the first media stream.

Field computing device 4, with the received second media stream and the originally captured first media stream, may superimpose (76) the received second media stream on the first media stream. Field computing device 4 may perform the superimposing based at least in part on aligning the timing information of the second media stream with the timing information of the first media stream. For instance, field computing device 4 may determine, based at least in part on the timing information of the second media stream, a starting time for the second media stream and an ending time for the second media stream. Field computing device 4 may then display the first media stream. Field computing device 4 may display the second media stream on top of the first media stream and simultaneously with the first media stream when the first media stream reaches a frame with timing information equal to the starting time of the second media stream, whether it is a frame number or a time. Field computing device 4 may then remove the second media stream from display when the first media stream reaches a frame with timing information equal to the ending time of the second media stream. In some examples, when the second media stream contains audio, field computing device 4 may further replace any audio in the first media stream with the audio of the second media stream.

In some examples, field computing device 4 may alter the size of the received second media stream. For instance, field computing device 4 may resize the received second media stream such that it is in the same aspect ratio as the recorded first media stream.

The superimposed video provides the field computing device with a treatment for the injury. For instance, where the first object is a gashed leg, the second object would be overlaid on top of the gashed leg, and would appear to move along the gashed leg in a way necessary for treatment of the gashed leg to occur, such as a movement to suture the wound. By performing the superimposing locally on field computing device 4 rather than field computing device 4 receiving a full media stream of the treatment over a low-bandwidth node network, field computing device 4 is able to receive a quality instructional treatment in a shorter time than if field computing device 4 waited for the entirety of a full media stream to be received.

Figure 5:
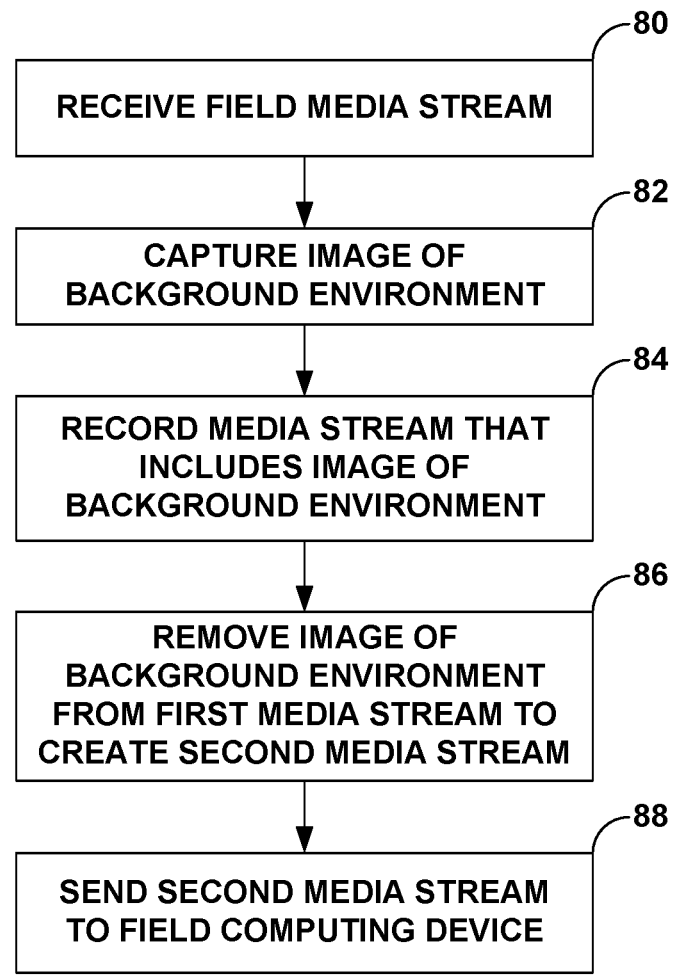
FIG. 5 is a flow diagram illustrating example operations of a central computing device that implements location techniques in accordance with one or more aspects of this disclosure.

FIG. 5 is a flow diagram illustrating example operations of a central computing device that implements location techniques in accordance with one or more aspects of this disclosure. The techniques of FIG. 5 may be performed by one or more processors of a computing device, such as central computing device 14 illustrated in FIG. 1 and/or FIG. 3. For purposes of illustration only, the techniques of FIG. 5 are described within the context of central computing device 14 of FIG. 1, although computing devices having configurations different than that of central computing device 14 may perform the techniques of FIG. 5.

In some examples, central computing device 14 may receive (80) a field media stream from a field computing device (e.g., field computing device 4 of FIG. 1). The field media stream may include timing information. In such examples, central computing device 14 may include timing information in the second media stream such central computing device 14 may align the timing information of the second media stream to the timing information of the field media stream. The timing information may include a time corresponding to the time that the field media stream begins, such as the time of day or the 0:00:00 indication, and a time corresponding to the time that the field media stream ends, such as the time of day later than the first time of day or the time in the form of #:##:##, wherein the #'s indicate numbers describing the length of the field media stream. In some instances, the timing information may instead or additionally include frame numbers.

In accordance with techniques of this disclosure, central computing device 14 may first capture (82) an image of a background environment (e.g., background environment 20 of FIG. 1), possibly utilizing camera 16. The background environment may be local to central computing device 14. For instance, the background environment may be any background environment, such as a solid-colored or patterned background "stage" or a general room containing various objects, among other things.

Central computing device 14 may then record (84) a first media stream, possibly utilizing camera 16. The first media stream may include at least a portion of the image of the previously captured background environment and at least one movement of an object (e.g., image of the medical expert's hand) through said background environment.

Central computing device 14 may remove (86) the image of background environment 20 from the first media stream to create a second media stream. The second media stream, accordingly, may only include the at least one movement of the object through the background environment without actually including the image of the background environment. By removing the image of the background environment, the second media stream will have a smaller size than the first media stream, allowing it to cross a low-bandwidth node network quicker and more efficiently. In some examples, central computing device 14 may further replace the object in the second media stream with a digital image different than the object. For instance, central computing device 14 may replace the object in the second media stream with a vector graphic, an arrow graphic, or a low-resolution representation of the object, such as a digital hand or pointer object.

The image of the background environment may be removed from the first media stream in any way suitable for the techniques described herein. For instance, if the background environment is a solid color, central computing device 14 may detect a pixel color value present in the image of the background environment and remove any pixel from each frame of the first media stream that matches or approximately matches (taking into account shading) the detected pixel color value of the pixels in the image of the background environment. If the background environment is a patterned background or a general room, the color-removal process may be repeated for each color found in the image of the background environment. In other examples, central computing device 14 of central computing device 14 may compute a depth at which the background environment lies in the image of the background environment. Central computing device 14 may then remove all objects from the first media stream found at that depth, leaving only the newly introduced object in the second media stream. These are merely examples of how the background environment may be removed from the first media stream. Any other technique available that results in the removal of the background environment from the first media stream may be utilized in accordance with the techniques of the current disclosure.

For instance, in another example of removing the image of background environment 20 from the second media stream, central computing device 14 may store a set of one or more object patterns. Each object pattern in the set of one or more object patterns may be one of a possible shape or a possible color of a possible configuration of the at least one object. Central computing device 14 may determine one or more portions of the first media stream that match an object pattern of the set of one or more object patterns. For each frame of the at least one frame of the first media stream, central computing device 14 may remove each pixel of the first media stream that is outside of the one or more portions that match the object pattern. For example, central computing device 14 may store different possible shapes and colors of hands. Central computing device 14 may attempt to find a portion of the second media stream that matches one of the object patterns containing possible shapes and colors of hands. Determining that the found portion is a hand, central computing device 14 may remove the pixels in the second media stream that are outside of the found portion, leaving only the hand in the second media stream.

In another example of removing the image of background environment 20 from the second media stream, central computing device 14 may, for each frame of at least one frame of the second media stream, compare the respective frame of the first media stream to the image of the background environment. Central computing device 14 may then remove each pixel of the second media stream with a color value equal to a color value of a corresponding pixel value in the image of the background environment. For instance, if camera 16 is in a fixed position, the background environment will not change between the image of the background environment and the filming of the second media stream. As such, if object 22 is in the middle of the second media stream, the pixel in the top-left corner of the second media stream may have a color value equal to the pixel in the top-left corner of the image of the background environment. As such, this pixel may be removed. Removing each matching pixel from each frame of the second media stream may leave only object 22 in the second media stream.

Central computing device 14 may then send (88) the second media stream and the timing information of the second media stream to the field computing device. In instances where image capture module 58 utilizes a microphone of camera 16 to capture audio data, the second media stream may further include the audio stream containing the captured audio data.

For instance, in aligning the timing information, central computing device 14 may determine, based at least in part on the timing information of the field media stream, a starting time of the field media stream and an ending time of the field media stream. Central computing device 14 may then determine a starting time for the second media stream and an ending time for the second media stream. The starting time for the second media stream may be between the starting time of the field media stream and the ending time of the field media stream. Further, the ending time for the second media stream may be after the starting time of the second media stream and before the ending time of the field media stream. As such, the timing information of the second media stream would be within the timing information of the field media stream and using the same time units as the field media stream.

In some examples, central computing device 14 may further alter the size of the second media stream. For instance, image alteration module 60 may resize the second media stream such that the aspect ratio of the second media stream matches an aspect ratio of the field media stream.

By way of example, and not limitation, such computer-readable storage media can include RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium may include a non-transitory medium. The term "non-transitory" indicates that the storage medium is not embodied in a carrier wave or a propagated signal. In certain examples, a non-transitory storage medium may store data that can, over time, change (e.g., in RAM or cache).

Various examples of the disclosure have been described. Any combination of the described systems, operations, or functions is contemplated. These and other examples are within the scope of the following claims.

The invention claimed is:

1. A method comprising:
   capturing, by a central computing device, an image of a background environment, wherein the background environment is local to the central computing device;
   recording, by the central computing device, a first media stream, wherein the first media stream includes at least a portion of the image of the background environment, and wherein the first media stream further includes at least one movement of a representation of at least one object through the background environment; and
   removing, by the central computing device, the image of the background environment from the first media stream to create a second media stream, wherein the second media stream includes the at least one movement of the at least one object through the background environment without the image of the background environment, wherein removing the image of the background environment from the first media stream comprises:
      detecting, by the computing device, one or more pixel color values present in the image of the background environment; and
      for each frame of at least one frame of the first media stream, removing, by the computing device, each pixel with a color value that matches one of the detected one or more pixel color values.

2. The method of claim 1, further comprising:
   receiving, by the central computing device, a field media stream from a field computing device, wherein the field media stream includes timing information.

3. The method of claim 2, further comprising:
   aligning, by the central computing device, timing information of the second media stream with the timing information of the field media stream; and
   sending, by the central computing device, the second media stream and the timing information of the second media stream to the field computing device.

4. The method of claim 2, further comprising:
   resizing, by the central computing device, an aspect ratio of the second media stream to equal an aspect ratio of the field media stream.

5. The method of claim 1, further comprising:
   replacing, by the central computing device, the object in the second media stream with a digital image that is different than the object.

6. The method of claim 5, wherein the digital image is a vector graphic.

7. The method of claim 1, wherein the first media stream further includes an audio stream captured by a microphone operably connected to the central computing device, and wherein the audio stream is included in the second media stream.

8. The method of claim 1, wherein capturing the image of the background environment comprises capturing, by the central computing device using a camera operatively connected to the central computing device, the image of the background environment, and wherein recording the first media stream comprises recording, by the central computing device using the camera, the first media stream.

9. A non-transitory computer-readable storage medium storing instructions that, when executed, cause one or more processors of a central computing device to:
   capture an image of a background environment, wherein the background environment is local to the central computing device;
   record a first media stream, wherein the first media stream includes at least a portion of the image of the background environment, and wherein the first media stream further includes at least one movement of a representation of at least one object through the background environment; and
   remove the image of the background environment from the first media stream to create a second media stream, wherein the second media stream includes the at least one movement of the at least one object through the background environment without the image of the background environment, wherein the instructions that cause the one or more processors to remove the image of the background environment from the first media stream comprise instructions that, when executed, cause the one or more processors to:
      detect one or more pixel color values present in the image of the background environment; and
      for each frame of at least one frame of the first media stream, remove each pixel with a color value that matches one of the detected one or more pixel color values.

10. The non-transitory computer-readable storage medium of claim 9, wherein the instructions, when executed, further cause the one or more processors to:
    receive a field media stream from a field computing device, wherein the field media stream includes timing information.

11. The non-transitory computer-readable storage medium of claim 10, wherein the instructions, when executed, further cause the one or more processors to:
    align timing information of the second media stream with the timing information of the field media stream; and
    send the second media stream and the timing information of the second media stream to the field computing device.

12. The non-transitory computer-readable storage medium of claim 9, wherein the first media stream further includes an audio stream captured by a microphone operably connected to the central computing device, and wherein the audio stream is included in the second media stream.

13. The non-transitory computer-readable storage medium of claim 9, wherein the instructions that cause the one or more processors to capture the image of the background environment comprises instructions that, when executed, cause the one or more processors to capture, using a camera operatively connected to the central computing device, the image of the background environment, and wherein the instructions that cause the one or more processors to record the first media stream comprises instructions that, when executed, cause the one or more processors to record, using the camera, the first media stream.

14. A method comprising:
capturing, by a field computing device, a first media stream, wherein the first media stream includes timing information;
sending, by the field computing device and to a central computing device, the first media stream;
after sending the first media stream, receiving, by the field computing device and from the central computing device, a second media stream, wherein the second media stream includes at least one movement of a representation of at least one object without any images of a background environment of the at least one object, and wherein the second media stream further includes timing information corresponding to the timing information of the first media stream; and
superimposing, by the field computing device, the second media stream on the first media stream, wherein the superimposing is based at least in part on synchronizing the timing information of the second media stream with the timing information of the first media stream, wherein superimposing the second media stream on the first media stream comprises:
determining, by the field computing device and based at least in part on the timing information of the second media stream, a starting time for the second media stream and an ending time for the second media stream;
displaying, by the field computing device, the first media stream:
displaying, by the field computing device, the second media stream on top of the first media stream and simultaneously with the first media stream when the first media stream reaches a frame with timing information equal to the starting time of the second media stream; and
removing, by the field computing device, the second media stream from display when the first media stream reaches a frame with timing information equal to the ending time of the second media stream.

15. The method of claim 14, wherein the second media stream further includes an audio stream.

16. The method of claim 15, wherein superimposing the second media stream on the first media stream further includes replacing, by the field computing device, an audio stream of the first media stream with the audio stream of the second media stream.

17. The method of claim 14, wherein capturing the first media stream comprises capturing, by the field computing device using a camera operatively connected to the field computing device, the first media stream.

18. The method of claim 14, further comprising resizing, by the field computing device, an aspect ratio of the second media stream to equal an aspect ratio of the first media stream.

19. A non-transitory computer-readable storage medium storing instructions that, when executed, cause one or more processors of a field computing device to:
capture a first media stream, wherein the first media stream includes timing information;
send, to a central computing device, the first media stream;
after sending the first media stream, receive, from the central computing device, a second media stream, wherein the second media stream includes at least one movement of representation of at least one object without any images of a background environment of the at least one object, and wherein the second media stream further includes timing information corresponding to the timing information of the first media stream; and
superimpose the second media stream on the first media stream, wherein the superimposing is based at least in part on synchronizing the timing information of the second media stream with the timing information of the first media stream, wherein the instructions that cause the one or more processors to superimpose the second media stream on the first media stream comprises instructions that, when executed, cause the one or more processors to:
determine, based at least in part on the timing information of the second media stream, a starting time for the second media stream and an ending time for the second media stream;
display the first media stream;
display the second media stream on top of the first media stream and simultaneously with the first media stream when the first media stream reaches a frame with timing information equal to the starting time of the second media stream; and
remove the second media stream from display when the first media stream reaches a frame with timing information equal to the ending time of the second media stream.

20. The non-transitory computer-readable storage medium of claim 19, wherein the second media stream further includes an audio stream.

21. The non-transitory computer-readable storage medium of claim 20, wherein the instructions that cause the one or more processors to superimpose the second media stream on the first media stream further comprises instructions that, when executed, cause the one or more processors to replace an audio stream of the first media stream with the audio stream of the second media stream.

22. The non-transitory computer-readable storage medium of claim 19, wherein the instructions that cause the one or more processors to capture the first media stream comprises instructions that, when executed, cause the one or more processors to capture, using a camera operatively connected to the field computing device, the first media stream.

23. A method comprising:
capturing, by a central computing device, an image of a background environment, wherein the background environment is local to the central computing device;
recording, by the central computing device, a first media stream, wherein the first media stream includes at least a portion of the image of the background environment, and wherein the first media stream further includes at least one movement of a representation of at least one object through the background environment; and removing, by the central computing device, the image of the background environment from the first media stream to create a second media stream, wherein the second media stream includes the at least one movement of the at least one object through the background environment without the image of the background environment, wherein removing the image of the background environment from the first media stream comprises:

storing, by the central computing device, a set of one or more object patterns, wherein each object pattern in the set of one or more object patterns comprises one of a possible shape or a possible color of a possible configuration of the at least one object;

determining, by the central computing device, one or more portions of the first media stream that match an object pattern of the set of one or more object patterns; and for each frame of at least one frame of the first media stream, removing, by the central computing device, each pixel of the first media stream that is outside of the one or more portions of the first media stream that match the object pattern.

24. The method of claim 23, further comprising:
receiving, by the central computing device, a field media stream from a field computing device, wherein the field media stream includes timing information;
aligning, by the central computing device, timing information of the second media stream with the timing information of the field media stream; and
sending, by the central computing device, the second media stream and the timing information of the second media stream to the field computing device.

25. The method of claim 23, further comprising:
replacing, by the central computing device, the object in the second media stream with a digital image that is different than the object.

26. The method of claim 23, wherein the first media stream further includes an audio stream captured by a microphone operably connected to the central computing device, and wherein the audio stream is included in the second media stream.

27. The method of claim 23, wherein capturing the image of the background environment comprises capturing, by the central computing device using a camera operatively connected to the central computing device, the image of the background environment, and wherein recording the first media stream comprises recording, by the central computing device using the camera, the first media stream.

28. A non-transitory computer-readable storage medium storing instructions that, when
executed, cause one or more processors of a central computing device to:
capture an image of a background environment, wherein the background environment is local to the central computing device;
record a first media stream, wherein the first media stream includes at least a portion of the image of the background environment, and wherein the first media stream further includes at least one movement of a representation of at least one object through the background environment; and
remove the image of the background environment from the first media stream to create a second media stream, wherein the second media stream includes the at least one movement of the at least one object through the background environment without the image of the background environment, wherein the instructions that cause the one or more processors to remove the image of the background environment from the first media stream comprise instructions that, when executed, cause the one or more processors to:
store a set of one or more object patterns, wherein each object pattern in the set of one or more object patterns comprises one of a possible shape or a possible color of a possible configuration of the at least one object;
determine one or more portions of the first media stream that match an object pattern of the set of one or more object patterns; and
for each frame of at least one frame of the first media stream, remove each pixel of the first media stream that is outside of the one or more portions of the first media stream that match the object pattern.

29. The non-transitory computer-readable storage medium of claim 28, wherein
the instructions, when executed, further cause the one or more processors to:
receive a field media stream from a field computing device, wherein the field media stream includes timing information;
align timing information of the second media stream with the timing information of the field media stream; and
send the second media stream and the timing information of the second media stream to the field computing device.

30. The non-transitory computer-readable storage medium of claim 28, wherein
the first media stream further includes an audio stream captured by a microphone operably connected to the central computing device, and wherein the audio stream is included in the second media stream.

31. The non-transitory computer-readable storage medium of claim 28, wherein
the instructions that cause the one or more processors to capture the image of the background environment comprises instructions that, when executed, cause the one or more processors to capture, using a camera operatively connected to the central computing device, the image of the background environment, and wherein the instructions that cause the one or more processors to record the first media stream comprises instructions that, when executed, cause the one or more processors to record, using the camera, the first media stream.

32. A method comprising:
capturing, by a central computing device, an image of a background environment, wherein the background environment is local to the central computing device;
recording, by the central computing device, a first media stream, wherein the first media stream includes at least a portion of the image of the background environment, and wherein the first media stream further includes at least one movement of a representation of at least one object through the background environment; and
removing, by the central computing device, the image of the background environment from the first media stream to create a second media stream, wherein the second media stream includes the at least one movement of the at least one object through the background environment without the image of the background environment, wherein removing the image of the background environment from the first media stream comprises:
for each frame of at least one frame of the first media stream:
comparing, by the central computing device, the respective frame of the first media stream to the image of the background environment; and
removing, by the central computing device, each pixel of the first media stream with a color value equal to a color value of a corresponding pixel in the image of the background environment.

33. The method of claim 32, further comprising:
receiving, by the central computing device, a field media stream from a field computing device, wherein the field media stream includes timing information;
aligning, by the central computing device, timing information of the second media stream with the timing information of the field media stream; and
sending, by the central computing device, the second media stream and the timing information of the second media stream to the field computing device.

34. The method of claim 32, further comprising:
replacing, by the central computing device, the object in the second media stream with a digital image that is different than the object.

35. The method of claim 32, wherein the first media stream further includes an audio stream captured by a microphone operably connected to the central computing device, and wherein the audio stream is included in the second media stream.

36. The method of claim 32, wherein capturing the image of the background environment comprises capturing, by the central computing device using a camera operatively connected to the central computing device, the image of the background environment, and wherein recording the first media stream comprises recording, by the central computing device using the camera, the first media stream.

37. A non-transitory computer-readable storage medium storing instructions that, when executed, cause one or more processors of a central computing device to:
capture an image of a background environment, wherein the background environment is local to the central computing device;
record a first media stream, wherein the first media stream includes at least a portion of the image of the background environment, and wherein the first media stream further includes at least one movement of a representation of at least one object through the background environment; and
remove the image of the background environment from the first media stream to create a second media stream, wherein the second media stream includes the at least one movement of the at least one object through the background environment without the image of the background environment, wherein the instructions that cause the one or more processors to remove the image of the background environment from the first media stream comprise instructions that, when executed, cause the one or more processors to:
for each frame of at least one frame of the first media stream:
comparing, by the central computing device, the respective frame of the first media stream to the image of the background environment; and
removing, by the central computing device, each pixel of the first media stream with a color value equal to a color value of a corresponding pixel in the image of the background environment.

38. The non-transitory computer-readable storage medium of claim 37, wherein
the instructions, when executed, further cause the one or more processors to:
receive a field media stream from a field computing device, wherein the field media stream includes timing information;
align timing information of the second media stream with the timing information of the field media stream; and
send the second media stream and the timing information of the second media stream to the field computing device.

39. The non-transitory computer-readable storage medium of claim 37, wherein
the first media stream further includes an audio stream captured by a microphone operably connected to the central computing device, and wherein the audio stream is included in the second media stream.

40. The non-transitory computer-readable storage medium of claim 37, wherein
the instructions that cause the one or more processors to capture the image of the background environment comprises instructions that, when executed, cause the one or more processors to capture, using a camera operatively connected to the central computing device, the image of the background environment, and wherein the instructions that cause the one or more processors to record the first media stream comprises instructions that, when executed, cause the one or more processors to record, using the camera, the first media stream.

\* \* \* \* \*

UNITED STATES PATENT AND TRADEMARK OFFICE
CERTIFICATE OF CORRECTION

PATENT NO. : 10,026,509 B2
APPLICATION NO. : 15/174704
DATED : July 17, 2018
INVENTOR(S) : Judson Powers et al.

Page 1 of 1

It is certified that error appears in the above-identified patent and that said Letters Patent is hereby corrected as shown below:

In the Specification

Column 1, Line 4: Insert the following paragraph:
--STATEMENT REGARDING FEDERALLY SPONSORED RESEARCH OR DEVELOPMENT
This invention was made with government support under Contract No. W81XWH-15-C-0161 and Contract No. W81XWH-16-C-0195 awarded by the US Army. The government has certain rights in this invention.--

Signed and Sealed this
Ninth Day of October, 2018

Andrei Iancu
*Director of the United States Patent and Trademark Office*